US006399749B1

(12) United States Patent
Smith

(10) Patent No.: US 6,399,749 B1
(45) Date of Patent: Jun. 4, 2002

(54) α-N-ACETYLGALACTOSAMINIDASE FROM *CLOSTRIDIUM PERFRINGENS*

(75) Inventor: Daniel S. Smith, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 09/185,476

(22) Filed: Nov. 3, 1998

Related U.S. Application Data

(60) Provisional application No. 60/064,683, filed on Nov. 3, 1997.

(51) Int. Cl.[7] .......................... A23J 1/00; C07K 14/00; C07K 16/00; C07K 17/00

(52) U.S. Cl. ........................ 530/412; 435/183; 435/200

(58) Field of Search ........................... 530/412; 435/208

(56) References Cited

PUBLICATIONS

Levy et al. Purification and properties of alpha–N–acetyl-galactosaminidase from C.perfringens. J. Biol. Chem., 1980, vol. 255(24):11737–11742.*

Hoskins et al.*

Chen et al., Proc. Natl. Sci Counc B. ROC, vol. 13, No. 3, pp. 201–209, Jul. 1989.

Purification and Characterization of Blood Group A–Degrading Isoforms of alpha–N–Acetylgalactosaminidase From Ruminococcus Torques Strain IX–70, Lansing C. Hoskins, et al., The Journal of Biological Chemistry, vol. 272, No. 12, Mar. 21,1997, pp. 7932–7939.

Purification and Properties of alpha–N–Acetylgalactosaminidase from *Clostridium perfringens*; Gerald N. Levy and David Aminoff; The Journal of Biological Chemistry; vol. 255, No. 24, Dec. 1980; pp. 11737–11742.

* cited by examiner

*Primary Examiner*—Ponnathapu Achutamurthy
*Assistant Examiner*—Mawjunath Rao
(74) *Attorney, Agent, or Firm*—Kohn & Associates

(57) ABSTRACT

An isolated and purified α-N-acetyl-D-galactosaminidase from *Clostridium perfringens* is disclosed. A method for purifying and isolating the α-N-acetylgalactosaminidase from *Clostridium perfringens* by removing neuramidases is disclosed. A process for using the α-N-acetylgalactosaminidase from *Clostridium perfringens* in altering type A blood cells to type O blood cells is disclosed. A process for altering cells expressing blood group A epitope by using α-N-acetylgalactosaminidase isolated from *Clostridium perfringens* in altering the cells expressing blood group A epitope to cells expressing blood group O epitope is disclosed.

1 Claim, 8 Drawing Sheets

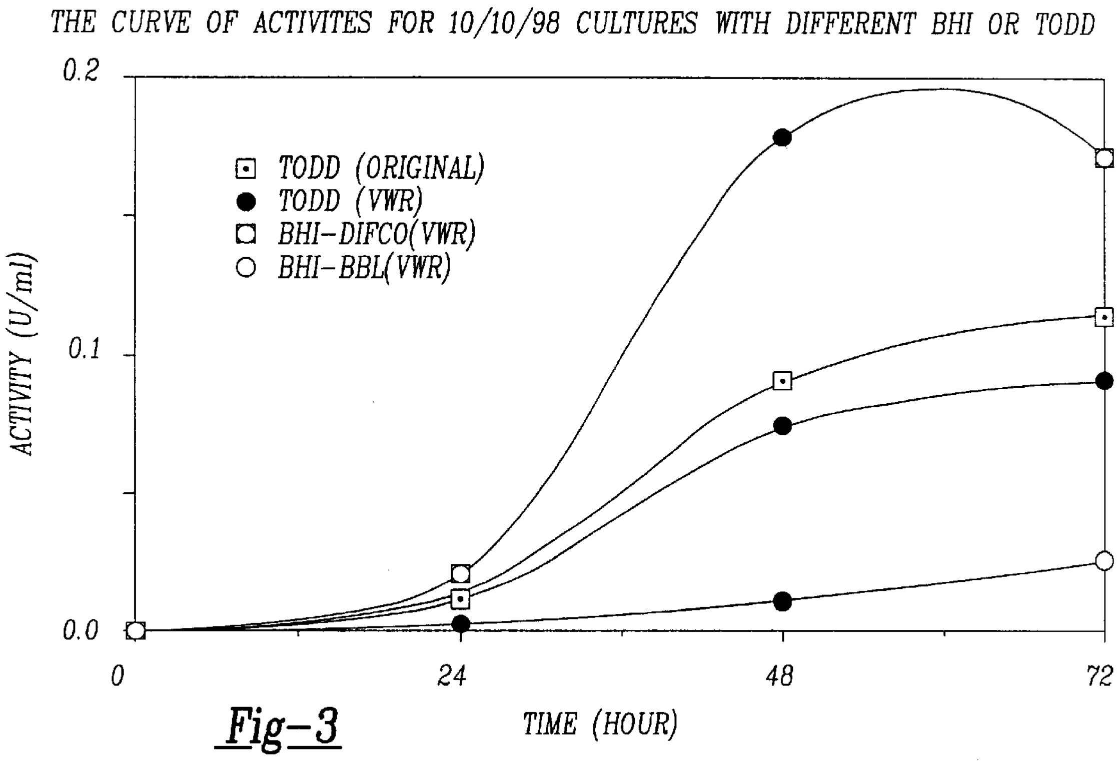
Fig-3
Fig-4
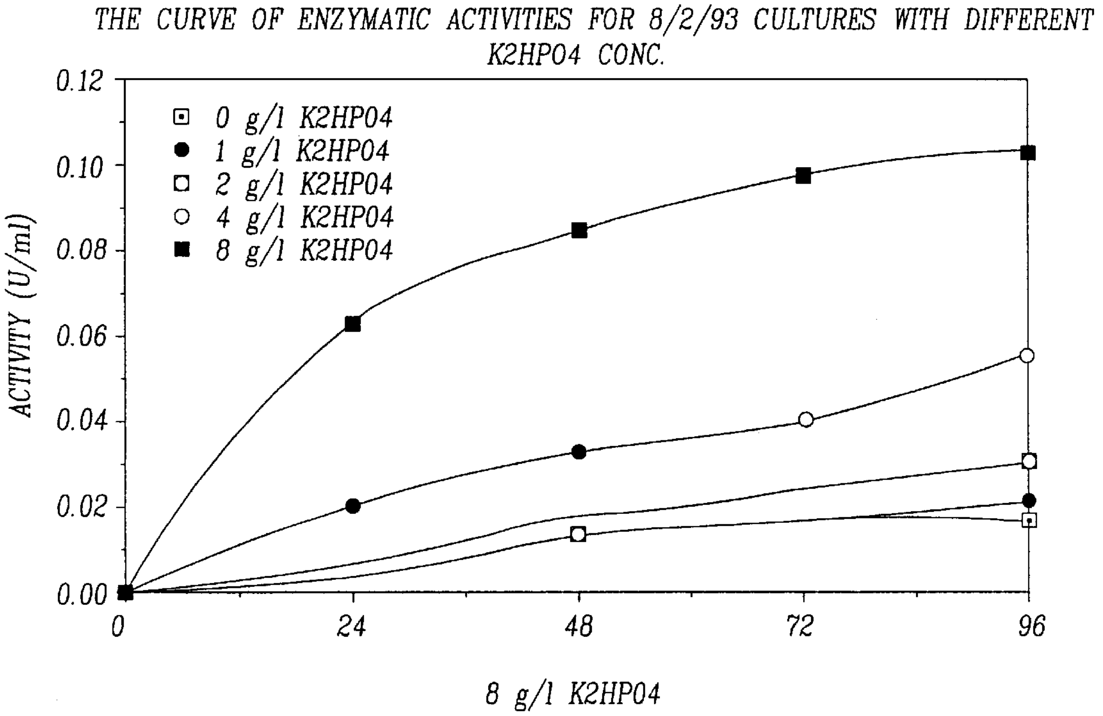

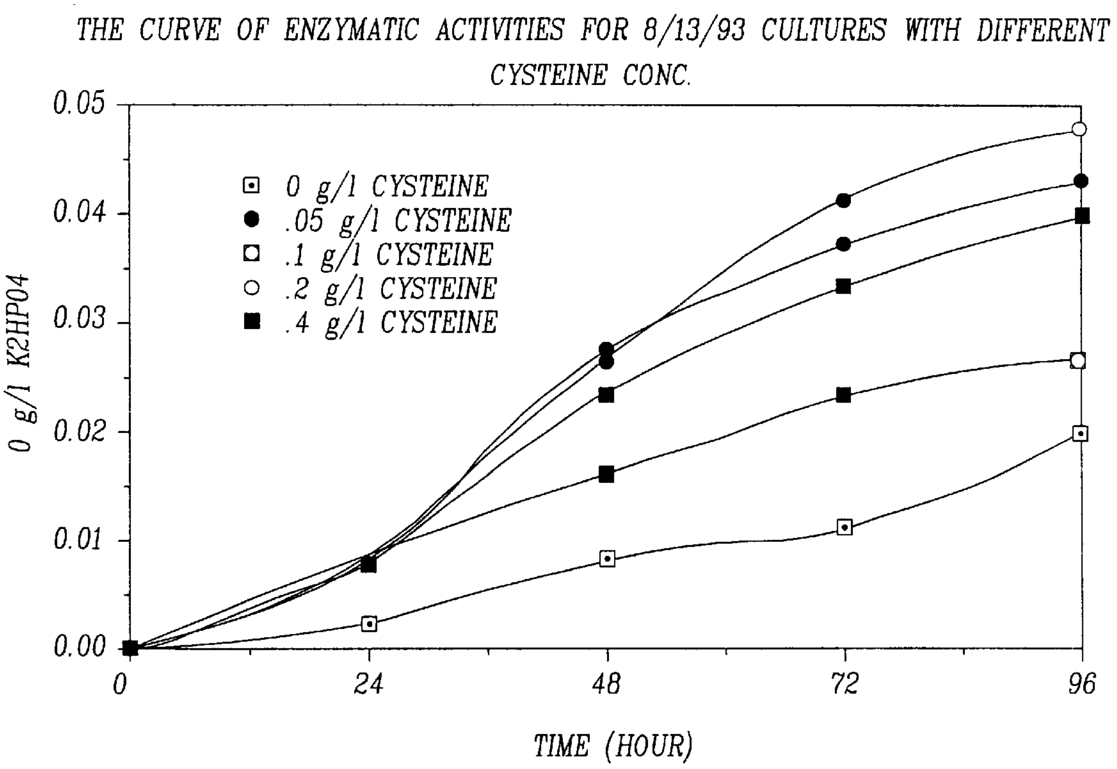
Fig-5
Fig-6
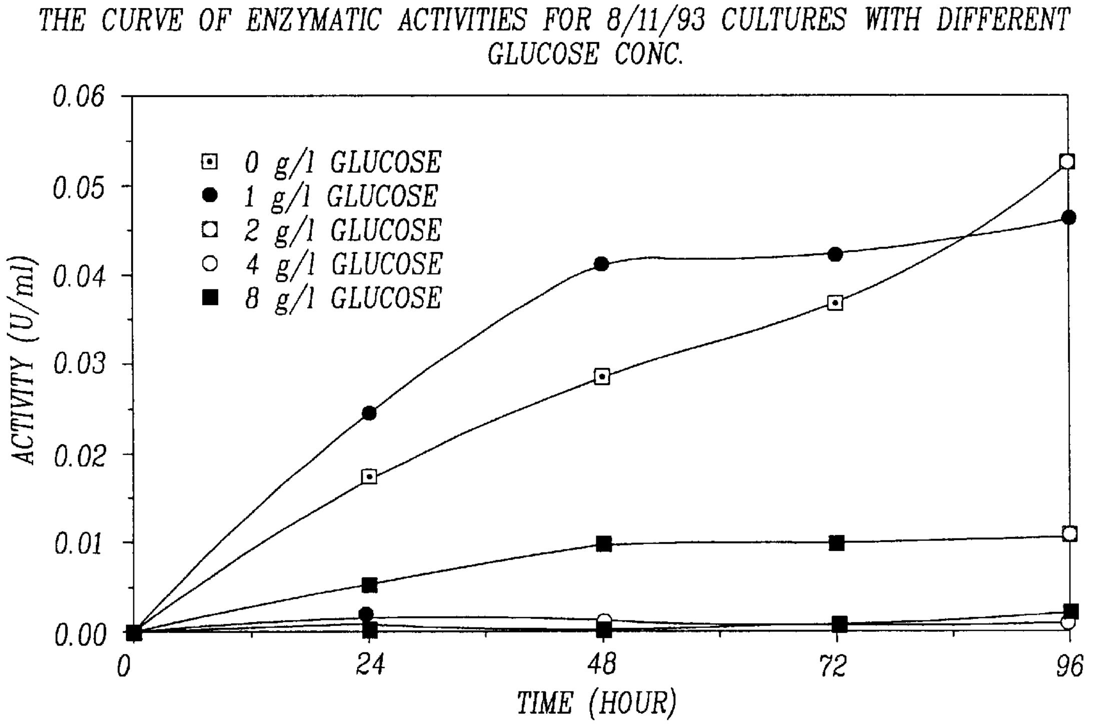

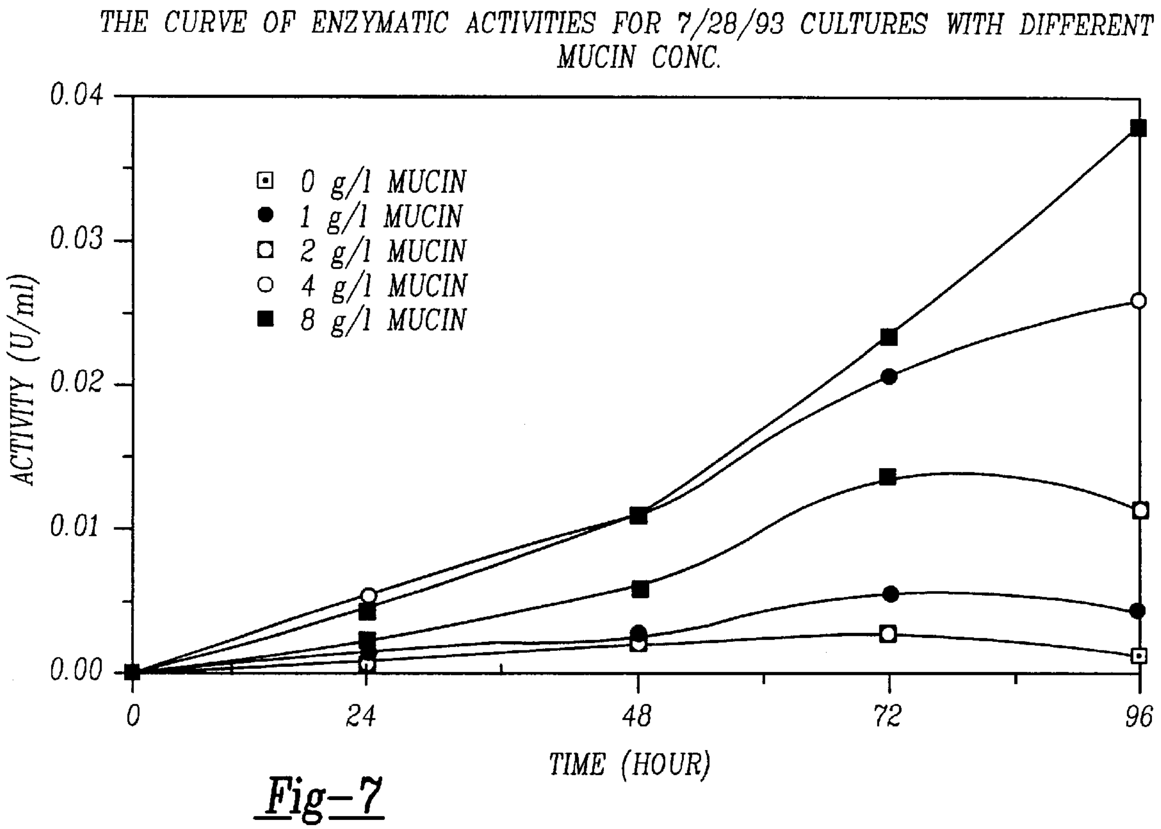
Fig-7
Fig-12
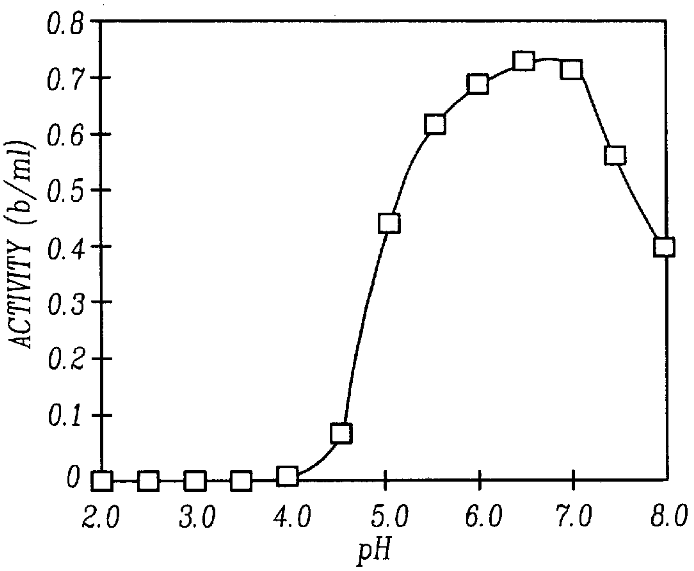

Fig-13
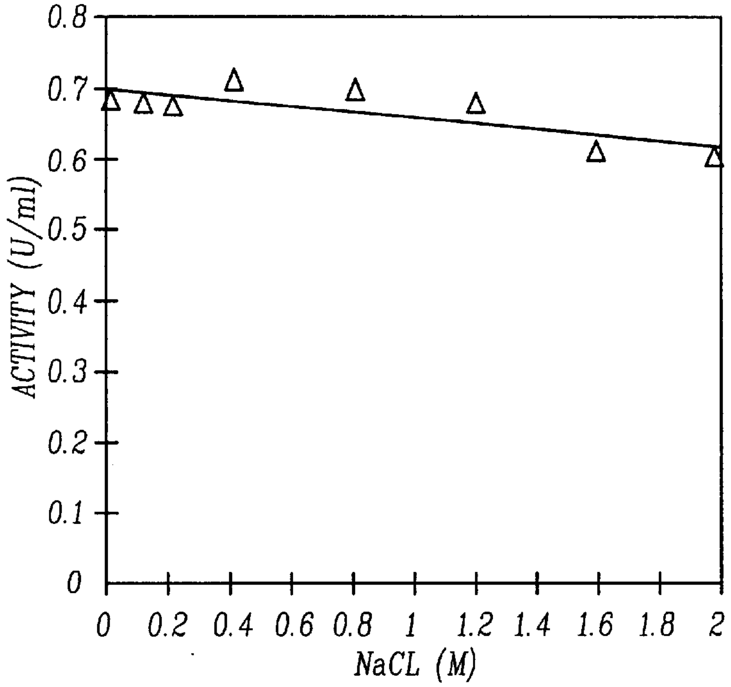
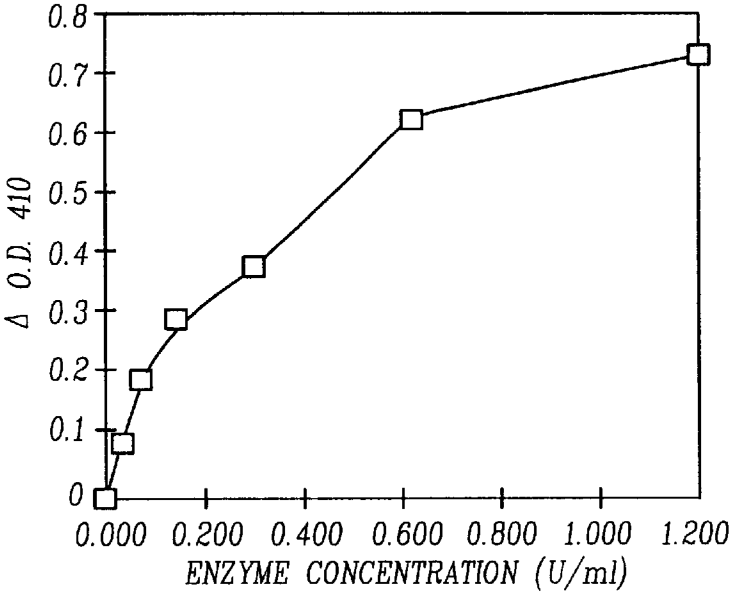
Fig-14

PRIMARY SEQUENCE

| | CALLED AMINE A | AMOUNT(S) (PMOTES) | CALLED AA'S |
|---|---|---|---|
| 1. | MET | 7.9 | |
| 2. | LYS | 4.4 | |
| 3. | VAL | 10.0 | |
| 4. | LEU | 10.5 | |
| 5. | GLY | 9.2 | |
| 6. | ASN | 15.7 | |
| 7. | TYR | 9.6 | |
| 8. | ILE | 11.1 | |
| 9. | GIN | 8.2 | |
| 10. | ARG | 8.0 | |
| 11. | ASN | 15.8 | |
| 12. | PHE | 9.9 | |
| 13. | HIS | 5.1 | |
| 14. | TYR | 8.9 | |
| 15. | ASP | 9.5 | |
| 16. | GLY | 7.1 | |
| 17. | LYS | 4.7 | |
| 18. | [x] | | |
| 19. | PHE | 5.8 | |
| 20. | TYR | 6.1 | |
| 21. | THR | 5.4 | |
| 22. | LYS | 3.5 | |
| 23. | [GIN] | | |
| 24. | PHE | 5.2 | ASN |
| 25. | [ASN] | 11.7 | |
| 26. | LYS | 3.6 | |
| 27. | PRO | 2.5 | GIN |
| 28. | ILE | 6.0 | |
| 29. | [x] | | |

REPETITIVE YIELD: [GLY-16 7.1 / GLY-5 9.2]$^{1/7}$ = 97.67% ESTIMATED REMAINING AFTER 27 RESIDGE(S) 4,871 PMOLE(S)

SEQUENCING PROGRAM USED: 03CBLT (ALL DATA FOR THIS ANALYSIS WILL BE ERASED FROM OUR COMPUTER AFTER ONE MONTH BUT WE WILL BE HAPPY TO COPY THE DATA ONTO ONE OF YOU DISKETTES IF DESIRED)

DISCUSSION SAMPLE NAME SMTPATH2

*Fig-15*

α-N-ACETYLGALACTOSAMINIDASE FROM *CLOSTRIDIUM PERFRINGENS*

This application claims benefit under 35 USC §119(e) of U.S. Provisional Application Serial No. 60/064,683, filed Nov. 3, 1997.

BACKGROUND OF THE INVENTION

1. Field of the Invention

The present invention relates to an improved method of isolating a purified α-N-acetylgalactosaminidase from *Clostridium perfringens* to be used in the conversion of erythrocytes to type O cells to render the cells useful for transfusion therapy.

2. Description of Related Art

The A, B, and H antigens are a clinically significant blood group (Landsteiner, 1901; Mollison et al, 1987). These antigens are terminal immunodominant monosaccharides on erythrocyte membrane glycoconjugates (Harmening, 1989). High densities of these epitopes are present on erythrocyte membranes and antibodies bound to these antigens readily fix complement (Economidou et al., 1967; Romano and Mollison, 1987). Because these epitopes are ubiquitous in nature, immuno-potent and naturally occurring, complement fixing antibodies occur in individuals lacking these antigens, and transfusion of incompatible blood results in fatal hemolytic transfusion reactions (Fong et al., 1974; Schmidt, 1980).

Complex sugar chains in glycolipids and glycoproteins have often been implicated in the growth and development of eukaryotes (Wantanabe et al., 1976). In particular, complex sugar chains play an important part in the recognition of self in the immune system (Mollison, 1987). Glycosidases (both exoglycosidases and endoglycosidases) are enzymes which can modify carbohydrate membrane epitopes, thereby modulating the immune response (Goldstein et al., 1982).

U.S. Pat. Nos. 4,330,619, issued May 18, 1982; 4,427,777, issued Jan. 24, 1984; and 4,609,627, issued Sep. 2, 1986, all to Goldstein, relate to the enzymatic conversion of certain erythrocytes to type O erythrocytes. Since type O erythrocytes can be safely transfused into type A, type B, type A,B recipients, as well as O recipients, type O erythrocytes have significant value in transfusion therapy. The above-mentioned U.S. Pat. No. 4,609,627 discloses the conversion of certain sub-type A and A,B erythrocytes to type O erythrocytes utilizing an α-N-acetylgalactosaminidase fraction from fresh chicken livers. The patent also discusses the significant potential of such enzymes to be used in the conversion of type $A_2$ erythrocytes to type O erythrocytes or type $A_2$ erythrocytes to type B erythrocytes.

The α-N-acetylgalactosaminidase from domestic chickens is such an enzyme as described above which degrades the human blood group A epitope (Hata et al., 1992). Degradation of the blood group A antigen produces the H antigen, also known as blood group O. Blood group O red blood cells are generally universally transfusable within the ABO blood group system.

The enzyme α-N-acetylgalactosaminidase [EC 3.2.1.49] is a class of exoglycosidases that have been purified from both procaryotes and eucaryotes (McGuire et al., 1972; McDonald et al., 1972; Kadowaki et al., 1989; Itoh and Uda, 1984; Nakagawa et al., 1987; Kubo, 1989; Weissman et al., 1969; Weissman, 1972). Despite the use of this enzyme because of its ready availability from the livers of domesticated chickens, the use is limited. This is based on the lack of published reports regarding the use of commercially useful purification methods for making preparations having no detectable protease or other glycosidase activities along with proven homogeneity (Goldstein, 1984). The low pH optimum of chicken liver enzyme makes it less useful because large masses of enzyme are required. Additionally, red cells must be extensively washed to lower the pH so that the enzyme can efficiently convert red cells from type A to type O or type $A_2B$ to type B. Similar problems exist with preparations from other sources including *Clostridium perfringens* (McGuire et al, 1972). Critically, without a commercially viable method to provide enzymatic activity free of extraneous proteases, neuraminidase, and glycosidases, there is limited commercial value since the use of a nonhomogeneous enzyme preparation has the potential to damage erythrocyte membranes, therefore leading to poor in vivo viability. It would be particularly advantageous to be able to a isolate α-N-acetylgalactosaminidase from *Clostridium perfringens* free of contaminants, particularly neuraminidase, while also having additional properties.

It would therefore be useful to develop an α-N-acetylgalactosaminidase which is homogeneous and capable of enzymatic activity against the blood group A epitope.

SUMMARY OF THE INVENTION

According to the present invention, an isolated and purified α-N-acetyl-D-galactosaminidase from *Clostridium perfringens* is disclosed. A method for purifiying and isolating the α-N-acetyl-D-galactosaminidase from *Clostridium perfringens* by removing neuramidases is disclosed. A process for using the α-N-acetyl-D-galactosaminidase from *Clostridium perfringens* in altering erythrocytes to type O erythrocytes is disclosed. A process for altering cells expressing blood group A epitope by using α-N-acetyl-D-galactosaminidase isolated from *Clostridium perfringens* in altering the cells expressing blood group A epitope to cells expressing blood group O epitope is disclosed.

DESCRIPTION OF THE DRAWINGS

Other advantages of the present invention will be readily appreciated as the same becomes better understood by reference to the following detailed description when considered in connection with the accompanying drawings wherein:

FIG. 3 shows a set of time courses showing BHI from Difco induced the highest expression;

FIG. 4 shows $K_2HPO_4$ having an optimal range of concentration between 4 and 8 gl;

FIG. 5 shows a cysteine concentration curve. Useful concentrations ranging from 0.05 to 0.4 g/l, concentration of 0.05 g/l seemed adequate for enzyme expression;

FIG. 6 is a glucose concentration curve; Lower glucose concentrations enhancing expression, a concentration range from 0 to 0.1 g/l being optimal;

FIG. 7 shows a porcine mucin concentration curve; higher mucin concentrations enhancing enzyme expression, a concentration greater than 4 g/l showing optimal expression;

FIG. 12 shows enzyme activity as a function of pH, measurements being performed as described in the Materials and Methods sections herein, all data points being the mean of three independent duplicate in determinations;

FIG. 13 shows enzyme activity as a function of ionic strength, measurements being performed as described in the Materials and Methods sections herein, all data points being the mean of three independent duplicate determinations;

FIG. 14 shows the degradation of the $A_2$ epitope as a function of enzyme concentration; Δ O.D.410 measuring the hydrolysis of the terminal N-acetyl-α-D-galactosamine from the blood group $A_2$ epitope, all data points being the mean of duplicate independent determinations; and FIG. 15 shows the N-terminal sequence of α-N-acetylgalactosaminidase.

DETAILED DESCRIPTION OF THE INVENTION

Figure 1:
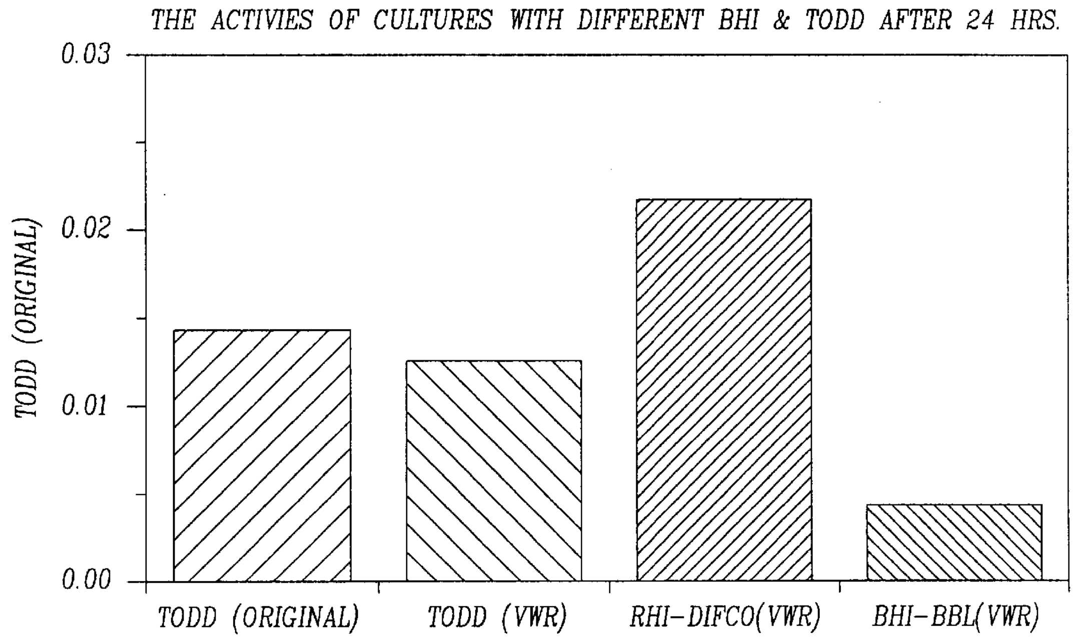
FIG. 1 is a bar graph showing the optimal expression occurred with Brain Heart Infusion (BHI), also shown in the Todd-Hewitt media used by Levy and Aminoff and the Difco brand BHI media.

The present invention provides a method of producing a purified α-N-acetylgalactosaminidase (SEQ ID No:1–7 and FIG. 15), and functional analogs thereof, from *Clostridium perfringens* which are free of neuraminidase activity. A detailed description of the isolation protocols and its properties are set forth in the Experimental Section.

By functional analogs, it is meant that an analog will generally be at least 70% homologous over any portion that is functionally relevant. In more preferred embodiments the homology will be at least 80% and can approach 95% homology to the α-N-acetylgalactosaminidase. The amino acid sequence of an analog may differ from that of the α-N-acetylgalactosaminidase when at least one residue is deleted, inserted or substituted. Differences in glycosylation can provide analogs. The molecular weight of the α-N-acetylgalactosaminidase can vary between the analog and the present invention due to carbohydrate differences.

Standard molecular biology techniques known in the art and not specifically described are generally followed as in Sambrook et al., *Molecular Cloning: A Laboratory Manual*, Cold Springs Harbor Laboratory, New York (1989, 1992), and in Ausubel et al., *Current Protocols in Molecular Biology*, John Wiley and Sons, Baltimore, Md. (1989). Additionally, standard methods in immunology known in the art and not specifically described are generally followed as in Stites et al. (eds), *Basic and Clinical Immunology* (85 Edition), Appleton & Lange, Norwalk, Conn. (1994) and Mishell and Shiigi (eds), *Selected Methods in Cellular Immunology*, W.H. Freeman and Co., New York (1980).

Cloning techniques are provided by the present invention. In general, recombinant α-N-acetylgalactosaminidase are superior to the native lysosomal enzymes for these applications.

Immunoassays are also provided by the present invention. In general, ELISAs are the preferred immunoassays employed to assess a specimen. Both polyclonal and moloclonal antibodies can be used in the assays. The specific assay to be used can be determined by one skilled in the art.

Antibody production is provided by the present invention. Antibodies may be prepared against the immunogen, or any portion thereof, for example a synthetic peptide based on the sequence. As stated above, antibodies are used in assays and are therefore used in determining if the appropriate enzyme has been isolated. Antibodies can also be used for removing enzymes from red cell suspensions after enzymatic conversion. Immunogens can be used to produce antibodies by standard antibody production technology well known to those skilled in the art as described generally in Harlow and Lane, *Antibodies: A Laboratory Manual*, Cold Springs Harbor Laboratory, Cold Spring Harbor, N.Y., 1988 and Borrebaeck, *Antibody Engineering—A Practical Guide*, W. H. Freeman and Co., 1992. Antibody fragments may also be prepared from the antibodies and include Fab, $F(ab')_2$, and Fv by methods known to those skilled in the art.

The enzyme obtained by the method of the present invention is characterized as having the following:

1. Homogeneous by SDS-PAGE
2. Molecular weight by SDS-PAGE of approximately 72.1 kDa.
3. Molecular weight by molecular sieve chromatography of approximately 57.5 kDa.
4. Specific activity of approximately 40.54 U $mg^{-1}$ $min^{-1}$ using 1 mM PNP-N-acetylyl-α-D-galactosaminide as a substrate and BSA as a protein standard in a BioRad Protein assay.
5. An approximate pH optimum of 6.5 to 7.0
6. Undetectable neuraminidase activity in the tested assay systems
7. Low to undetectable protease activity.
8. Activity against the blood group $A_2$ on erythrocyte membranes using an ELISA assay.

These properties make the enzyme isolated and purified by the method of the present invention useful in enzymatic conversion technology to produce type O red blood cells.

Briefly the method for isolating and purifying the enzyme begins by expressing the enzyme in stationary cultures. After 92 hours the medium is harvested by centrifugation. The mineral oil overlay is separated from the medium in a separatory funnel and the enzyme purified from the cell free expired medium.

More specifically, the procedures of *Clostridium perfringens* A-N-acetylgalactosaminidase purification generally include the following steps: 1)obtaining a *Clostridium perfringens* culture; 2) conducting a $(NH_4)_2SO_4$ precipitation; 3) pass the preparation through a S-200 (I) column; 4) load the preparation into a separation column sold under the trademark DEAE SEPHADEX A-50 (I) column; 5) load the preparation into a the exchanger sold under the trademark PBE 94 exchanger; 6) load the preparation into a SP Sephadex C-50 column; 7) load the preparation into a separation column sold under the trademark nDEAE Sephadex A-50 (II) column; and 8) load the preparation into a column sold under the trademark HYDROXYAPATITE TYPE I column.

Figure 2:
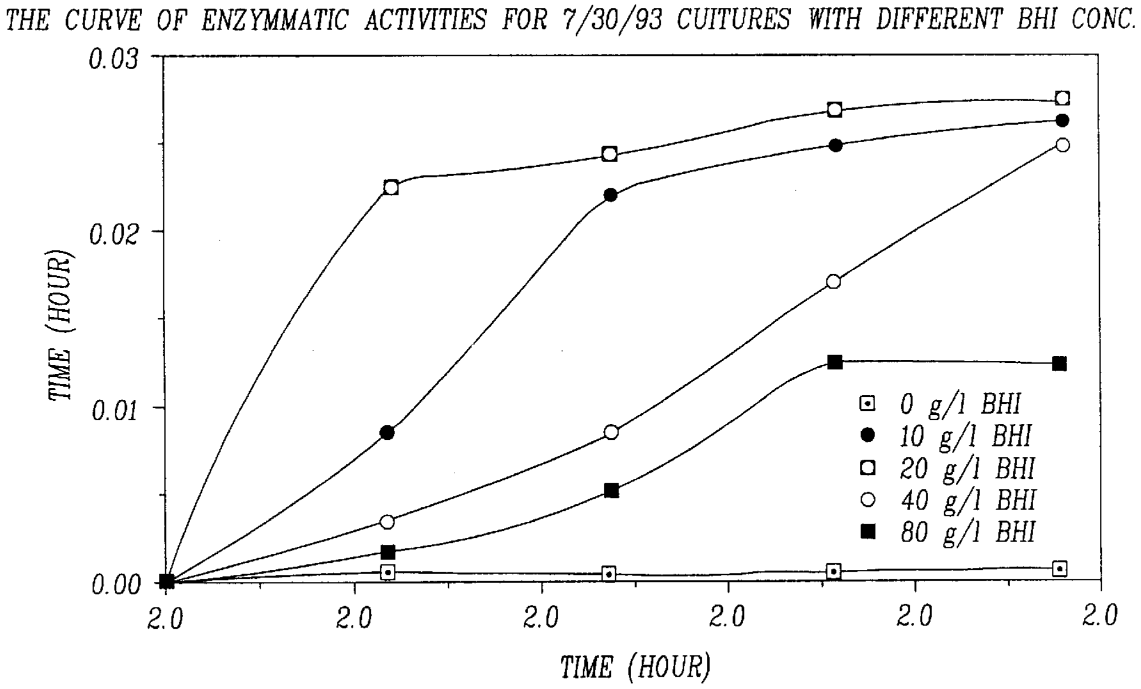
FIG. 2 shows enzyme expression as a function of BHI concentration, optimal concentrations ranging from 20 to 80 g/l.

Various buffers can be used for the purification. Initially, a cell culture is cultured, as previously described (Levy and Aminoff, 1980) with a modification. It was found that these methods are not beneficial because little or no enzymatic activity was observed using the ATCC strain and media conditions described by those authors. Therefore, Brain Heart Infusion (BHI) is substituted for Todd-Hewitt broth because it was found that BHI provides optimal expression as is shown in FIG. 1. The BHI media contains BHI, $K_2HPO_4$, cysteine, glucose, and porcine gastric mucin. Optimal concentration of the components of the BHI media are as follows: BHI concentration was optimal in the range of 20 to 80 g/l (FIG. 2) further, it was found that BHI from Difco induced the greatest expression (FIG. 3); $K_2HPO_4$ is added to the media to maintain pH with a useful range of 4 to 8 g/l (FIG. 4); cysteine has useful concentrations in the range of 0.05 to 0.4 g/l (FIG. 5); lower glucose concentrations enhanced expression and a concentration range from O to 0.1 g/l is optimal (FIG. 6); and higher porcine mucin concentration enhanced enzyme expression with concentrations higher than 4 g/l being optimal (FIG. 7).

The cell culture is separated from the mineral oil and centrifuged. The cell-free supernatant is brought to 70% saturation with solid $(NH_4)_2SO_4$, and is stirred gently at 4° C. for two hours. The precipitate is collected by centrifugation and then dissolved in $1/50^{th}$ of the starting volume in 50 mM Na acetate buffer, pH 5.0, containing 1.0 mM DTT, 0.1% (v/v) Tween 80 and 0.01% (w/v) $NaN_3$. The suspension is then centrifuged to collect the precipitate-free supernatant.

The supernatant is then applied to a column of sold under the trademark SEPHACRYL S-200 which is equilibrated in a Na acetate buffer. The column is developed with equilibration buffer at 4° C. Fractions are obtained which have enzyme activity and are then pooled and dialyzed against a buffer.

This dialyzed pool is applied to a column of DEAE Sephadex A-50 which is equilibrated in a Tris-HCl buffer at 4° C. Again fractions containing enzyme activity are pooled and dialyzed against a buffer.

The dialyzed pool is then applied to a column of PBE 94 chromatofocusing resin which is equilibrated. Elution is accomplished by developing the column with Polybuffer 74 solution. Fractions containing enzyme activity are pooled and dialyzed against a sodium acetate buffer.

Then the dialyzed preparation is applied to a column of column sold under the trademark name "SP SEPHADEX" C-50 which is equilibrated in a sodium acetate buffer. The effluent is collected and retained upon which time the column is washed with sodium acetate buffer. The effluent and wash are combined and dialyzed against a Tris-HCl buffer.

Next, the dialyzed pool is applied to a column of sold under the trademark name "DEAE SEPHADEX" A-50 which is equilibrated in a Tris-HCl buffer. Fractions containing enzyme activity are pooled. This enzyme pool was dialyzed and a $K_2HPO_4$ buffer and then applied to a BioScale Ceramic Hydroxyapatite, Type I column for HPLC. Fractions obtained from this are retained and pooled and then stored at 4° C.

Protein concentrations are quantitated with the Bio-Rad protein assay, or any assay known by one skilled in the art which quantitates protein concentrations. Enzymatic activity is determined by measuring the production of p-nitrophenol (PNP) from PNP-N-acetyl-α-D-galactosaminide. Neuraminidase activity is then measured using 4-MU-α-N-acetylneuraminic acid by an adaptation of the method of Dean et al. (1977).

The above discussion provides a factual basis for the use of α-N-acetyl-D-galactosaminidase. The methods used with and the utility of the present invention can be shown by the following non-limiting examples and accompanying FIGS.

The following Experimental section provides a specific extraction process and analytical procedure characterizing the derived purified enzyme.

EXPERIMENTAL EVIDENCE

General Methods

General methods in molecular biology: Standard molecular biology techniques known in the art and not specifically described are generally followed as in Sambrook et al., *Molecular Cloning: A Laboratory Manual*, Cold Springs Harbor Laboratory, New York (1989, 1992), and in Ausubel et al., *Current Protocols in Molecular Biology*, John Wiley and Sons, Baltimore, Md. (1989). Polymerase chain reaction (PCR) is carried out generally as in *PCR Protocols: A Guide To Methods And Applications*, Academic Press, San Diego, Calif. (1990). Reactions and manipulations involving other nucleic acid techniques, unless stated otherwise, are performed as generally described in Sambrook et al., 1989, *Molecular Cloning: A Laboratory Manual*, Cold Spring Harbor Laboratory Press, and methodology as set forth in U.S. Pat. Nos. 4,666,828; 4,683,202; 4,801,531; 5,192,659 and 5,272,057 and incorporated herein by reference. In-situ (In-cell) PCR in combination with Flow Cytometry can be used for detection of cells containing specific DNA and mRNA sequences (Testoni et al, 1996, Blood 87:3822. ) Additionally, cloning is carried out as generally described in *Molecular Cloning: A Laboratory Manual*, Cold Spring Harbor Laboratory Press.

General methods in immunology: Standard methods in immunology known in the art and not specifically described are generally followed as in Stites et al.(eds), Basic and Clinical Immunology (8th Edition), Appleton & Lange, Norwalk, Conn. (1994) and Mishell and Shiigi (eds), Selected Methods in Cellular Immunology, W. H. Freeman and Co., New York (1980).

Immunoassays

In general, ELISAs are the preferred immunoassays employed to assess a specimen. ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, *Molecular Cloning: A Laboratory Manual*, Cold Springs Harbor, N.Y., 1989

Antibody Production

Antibody Production: Antibodies may be either monoclonal, polyclonal or recombinant. Conveniently, the antibodies may be prepared against the immunogen or portion thereof for example a synthetic peptide based on the sequence, or prepared recombinantly by cloning techniques or the natural gene product and/or portions thereof may be isolated and used as the immunogen. Immunogens can be used to produce antibodies by standard antibody production technology well known to those skilled in the art as described generally in Harlow and Lane, *Antibodies: A Laboratory Manual*, Cold Spring Harbor Laboratory, Cold Spring Harbor, N.Y., 1988 and Borrebaeck, *Antibody Engineering—A Practical Guide*, W. H. Freeman and Co., 1992. Antibody fragments may also be prepared from the antibodies and include Fab, $F(ab')_2$, and Fv by methods known to those skilled in the art.

For producing polyclonal antibodies a host, such as a rabbit or goat, is immunized with the immunogen or immunogen fragment, generally with an adjuvant and, if necessary, coupled to a carrier; antibodies to the immunogen are collected from the sera. Further, the polyclonal antibody can be absorbed such that it is monospecific. That is, the sera can be absorbed against related immunogens so that no cross-reactive antibodies remain in the sera rendering it monospecific.

For producing monoclonal antibodies the technique involves hyperimmunization of an appropriate donor with the immunogen, generally a mouse, and isolation of splenic antibody producing cells. These cells are fused to a cell having immortality, such as a myeloma cell, to provide a fused cell hybrid which has immortality and secretes the required antibody. The cells are then cultured, in bulk, and the monoclonal antibodies harvested from the culture media for use.

For producing recombinant antibody (see generally Huston et al, 1991; Johnson and Bird, 1991; Mernaugh and Mernaugh, 1995), messenger RNAs from antibody producing B-lymphocytes of animals, or hybridoma are reverse-transcribed to obtain complimentary DNAs (CDNAs). Antibody cDNA, which can be full or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody. Antibody cDNA can also be obtained by screening pertinent expression libraries.

The antibody can be bound to a solid support substrate or conjugated with a detectable moiety or be both bound and conjugated as is well known in the art. (For a general discussion of conjugation of fluorescent or enzymatic moieties see Johnstone & Thorpe, *Immunochemistry in Practice*, Blackwell Scientific Publications, Oxford, 1982.) The binding of antibodies to a solid support substrate is also well known in the art. (see for a general discussion Harlow & Lane *Antibodies: A Laboratory Manual*, Cold Spring Harbor Laboratory Publications, New York, 1988 and Borrebaeck, *Antibody Engineering—A Practical Guide*, W. H. Freeman and Co., 1992) The detectable moieties contemplated with the present invention can include, but are not limited to, fluorescent, metallic, enzymatic and radioactive markers such as biotin, gold, ferritin, alkaline phosphatase, α-galactosidase, peroxidase, urease, fluorescein, rhodamine, tritium, $^{14}C$ and iodination.

Recombinant Protein Purification

Marshak et al, "trategies for Protein Purification and Characterization. A laboratory course manual." CSHL Press, 1996.

EXAMPLES

The following is the detailed description of the protocol of the present invention for isolating a purified α-N-acetylgalactosaminidase from *Clostridium perfringens* free of neuraminidase activity to be used in the conversion of erythrocytes to type O cells to render the cells useful for transfusion therapy. The properties of the isolated enzyme are also provided.

Methods and Materials

Materials

*Clostridium perfringens* was obtained from the American Type Culture Collection (ATCC), Rockville, Mass. Media were purchased from Difco Laboratories, Detroit, Mich. Protein assay dye reagent was obtained from Bio-Rad, Hercules, Calif. An anaerobic system and BBL GasPak Plus were purchased from Becton Dickinson and Company, Cockeysville, Md. SDS polyacrylamide gels and HPLC (high pressure liquid chromatography) columns were purchased from Bio-Rad, Hercules, Calif. Dithiothreitol (DTT) and $K_2HPO_4$ were acquired from Fisher Biotech, Pittsburgh, Pa. Porcine gastric mucin, L-cysteine, glucose, bovine serum albumin (BSA), PolyBuffer 74, substrates (4-methylumbel-liferyl-α-D-N-acetylneuraminic acid, PNP- and ONP-N-acetyl-α-D-galactosaminide), all other chemicals, and chromatography resins sold under the trademark name SEPHACRYL S-200, DEAE SEPHADEX A-50, PBE 94 and SP SEPHADEX C-50were obtained from Sigma Chemical Company, St. Louis, Mo. Endoprotease substrates were purchased from Boehringer Mannheim, Indianapolis, Ind.

Methods

Bacterial Culture: *Clostridium perfringens* was cultured as previously described (Levy and Aminoff 1980), however, Brain Heart Infusion (BHI) was substituted for Todd-Hewitt broth in the formulation. A lyophilized vial of *Clostridium perfringens* strain ATCC 10543 was suspended in 1.0 ml of prewarmed and prereduced BHI media containing 40 g/l BHI, 8 g/l $K_2HPO_4$, 0.05 g/l cysteine, 1 g/l glucose and 5 g/l porcine gastric mucin. The suspension was added to 10 ml of warm reduced media and incubated at 37° C. After ten to twelve 24-hour passages, 10 ml of culture was added to 2.5 liters of warmed, reduced media overlaid with 400 ml of mineral oil. Pick up 1 ml aliquot from the culture flask and assay the α-N-acetylgalactosaminidase activity every 24 hours during the incubation. Plot the graph of the α-N-acetylgalactosaminidase activity v.s. time to determine the maximal enzyme activity. The mineral oil maintained an anaerobic environment. The bacteria were grown in standing culture at 37° C. for approximately 72 to 96 hours. Enzyme production was monitored, and the culture was harvested after plateauing.

Purification of α-N-acetylgalactosaminidase

Step 1. The culture was separated from mineral oil with a separatory funnel, and was centrifuged at 5,620×g for 30 min. at 4° C. The cell-free supernatant was brought to 70% saturation with solid $(NH_4)_2SO_4$, and was then stirred gently at 4° C. for 2 hours. The precipitate was collected by centrifugation (5,620×g, 2 hours, 4° C.), and was dissolved in 1/50th of the starting volume in 50 mM Na acetate buffer, pH 5.0, containing 1.0 mM DTT, 0.1%(v/v) Tween 80 and 0.01%(w/v) $NaN_3$. The suspension was then centrifuged at 5,620×X g for 60 min. at 4° C. to collect the precipitate-free supernatant.

Step 2. The supernatant was applied to a 5×90 cm column sold under the trademark name SEPHACRYL S-200 equilibrated in 50 mM Na acetate buffer, pH 5.0, containing 1.0 mM DTT, 0.1% Tween 80 and 0.01% $NaN_3$, and the column was developed with equilibration buffer at 4° C. Fractions containing enzyme activity were pooled and dialyzed against 10 mM Tris-HCI buffer, pH 8.0, containing 1.0 mM DTT, 0.1% Tween 80 and 0.01% $NaN_3$ at 40° C.

Step 3. The dialyzed pool was applied to a 1.5×20 cm column of sold under the trademark name DEAE SEPHADEX" A-50 equilibrated in 10 mM Tris-HCl buffer, pH 8.0, containing 1.0 mM DTT, 0.1% Tween 80 and 0.01% $NaN_3$ at 4° C. The elution was achieved by developing the column with a 200 ml linear gradient of 10mM Tris-HCI buffer, pH 8.0, containing 0 to 500 mM NaCl, 1.0 mM DTT, 0.1% Tween 80 and 0.01% $NaN_3$ at 4° C. Fractions containing enzyme activity were pooled and dialyzed against 20 mM MES buffer, pH 6.2, containing 1.0 mM DTT, 0.1% Tween 80 and 0.01% $NaN_3$ at 4° C.

Step 4. After dialysis, the pool was applied to a 1×30 cm column sold under the trademark PBE 94 chromatofocusing, equilibrated in 20 mM MES buffer, pH 6.2, containing 1.0 mM DTT, 0.1% Tween 80 and 0.01% $NaN_3$ at 4° C. Elution was accomplished by developing the column with Polybuffer 74 solution, pH 3.8 at 4° C. Fractions containing enzyme activity were pooled and dialyzed against 10 mM Na acetate buffer, pH 5.0, containing 1.0 mM DTT, 0.1% Tween 80 and 0.01% $NaN_3$ at 4° C.

Step 5. The dialyzed preparation was applied to a 1×5 cm column of SP Sephadex C-50 equilibrated in 10 mM Na acetate buffer, pH 5.0, containing 1.0 mM DTT, 0.1% Tween 80 and 0.01% $NaN_3$ at 4° C. The effluent was collected and retained, and the column was washed with 5 ml of 10 mM Na acetate buffer, pH 5.0, containing 1.0 mM DTT, 0.1% Tween 80 and 0.01% $NaN_3$. The effluent and wash were combined and dialyzed against 10 mM Tris-HCl, pH 8.0, containing 1.0 mM DTT, 0.1% Tween 80 and 0.01% $NaN_3$ at 4° C.

Step 6. The dialyzed pool was applied to a 1.5×5 cm column of DEAE Sephadex A-50 equilibrated in 10 mM Tris-HCl buffer, pH 8.0, containing 1.0 mM DTT, 0.1% Tween 80 and 0.01% $NaN_3$ at 4° C. The elution was achieved by developing the column with a 100 ml linear gradient of 10 mM Tris-HCl buffer, pH 8.0, containing 0 to 500 mM NaCl, 1.0 MM DTT, 0.1% Tween 80 and 0.01% $NaN_3$ at 4° C. Fractions with enzyme activity were pooled.

Step 7. The enzyme pool was dialyzed against 10 mM $K_2HPO_4$ buffer, pH 6.8, containing 1.0 mM DTT, 0.1% Tween 80 and 0.01% $NaN_3$ at 4° C., and applied to a Bio-Scale Ceramic Hydroxyapatite, Type 1 column for HPLC at room temperature. The enzyme was eluted with a continuous phosphate gradient of 10 to 400 mM $K_2HPO_4$. Fractions containing enzyme activity were pooled and stored at 4° C.

Characterization of α-N-acetylgalactosaminidases

Protein concentrations were quantitated with the Bio-Rad protein assay using BSA as a standard. Enzymatic activity was determined by measuring production of p-nitrophenol (PNP) from PNP-N-acetyl-α-D-galactosaminide. Enzyme aliquots were incubated in 200 μL of 40 mM $NaH_2PO_4$ buffer, pH 6.5, containing 1.0 mg $mL^{-1}$ BSA, 1.0 mM DTT, and 1.0 mM PNP-N-acetyl-α-D-galactosaminide, at 37° C. The reactions were quenched with 1.0 mL of 0.25 M $Na_2CO_3$ and the OD 405 nm was measured. One unit of activity was defined as 1.0 μmole of substrate hydrolyzed per minute. Neuraminidase activity was measured using 4-MU-α-N-acetylneuraminic acid by an adaptation of the method of Dean et al. (1977).

The pH optimum was determined by incubating enzyme aliquots in 20 mM $NaH_2PO_4$ and 20 mM Na citrate, pH 2.0 to 8.0, containing, 1.0 mg $mL^{-1}$ BSA, 1.0 mM DTT and 2.5 mM PNP-N-acetyl-α-D-galactosaminide at 37° C. The ionic strength optimum was determined by incubating aliquots of the enzyme in 2.5 mM $NaH_2PO_4$ buffer, pH 7.0, containing 1.0 mg $mL^{-1}$ BSA, 2.5 mM PNP-N-acetyl-α-D-galactosaminide and 0 to 2.0 M NaCl at 37° C. The $K_m$s for ONP- and PNP-N-acetyl-α-D-galactosaminide were determined by varying the substrate concentration in 50 mM $NaH_2PO_4$ buffer, pH 7.0, containing 1.0 mg $mL^{-1}$ BSA and 0.01k $NaN_3$, at 37° C. The native molecular weight was determined by applying a concentrated portion of the enzyme to a 1.5×40 cm column of Sephacryl S-200 equilibrated in 10 mM Tris-HCl buffer, pH 8.0, containing 150 mM NaCl, 1.0 mM DTT, 0.1% Tween 80 and 0.01% $NaN_3$. Enzyme activity was measured as a function of fraction number, and compared to native molecular weight standards. SDS (sodium dodecyl sulfate) polyacrylamide electrophoresis (SDS-PAGE) was performed by a method of Laemmli (1970), and the protein bands were developed with either Coomassie R-250 or zinc stain (Fernandez-Patron et al, 1992). Amino acid composition was analyzed on a Perkin Elmes (PE) ABD model 120A PTH Amino Acid Analyzer using UV detection. Aminopeptidase assays were performed by incubating aliquots of enzyme with 2.5 mM of various p-nitroaniline (PNA) substrates in 50 mM Na acetate, pH 6.0, containing 50 mM $NaH_2PO_4$, 1.0 mg $mL^{-1}$ BSA, and 0.01% $NaN_3$, at 37° C. (Macfarlane et al, 1988). The reactions were quenched with 1.0 ml of 0.25 M $Na_2CO_3$, and the OD at 405 nm was determined. One unit of aminopeptidase activity is defined as 1.0 μmole of PNA hydrolyzed per minute. Endoprotease assays were performed by an adaptation of the resorufin-labeled casein assay of Twining (1984). Blood group activity was determined with an enzyme linked immunosorbent assay (ELISA) as described by Hobbs et al. (1993).

Results

As shown in Table I, rapid purification of the enzyme was achieved with acceptable recoveries. Neuraminidase was the most undesirable contaminant that was efficiently removed by this purification scheme. The DEAE Sephadex A-50, PBE 94 chromatofocusing, and SP Sephadex C-50 columns removed the bulk of contaminating protein and neuramidase. Final purification was achieved by high pressure liquid chromatography (HPLC) on a Bio-Scale Ceramic Hydroxyapatite, Type I column. The specific activity of the purified enzyme ranged from 30.40 to 50.68 units milligram $protein^{-1}$ $minute^{31\ 1}$ (X=42.19, s.d.=10.53, n=3) with 1.0 mM PNP-N-acetyl-α-D-galactosaminide as the substrate. There was a 137 fold purification with an average recovery of 1.97%, Table 1. The enzyme was stable at 4° C. for over a year with less than 10% loss of activity.

Figure 8:
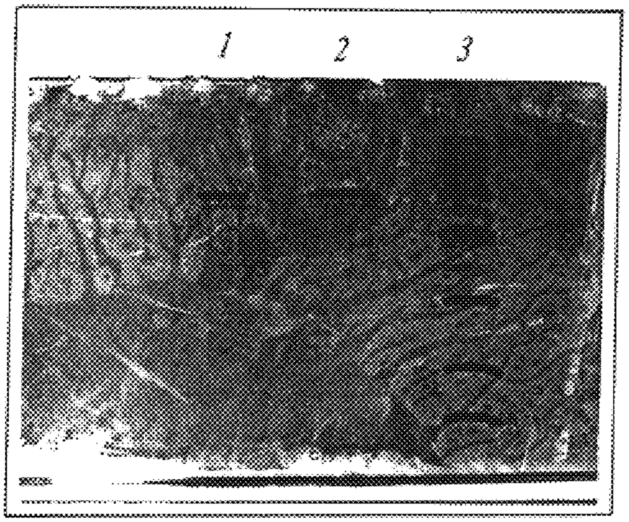
FIG. 8 shows an SDS-PAGE with lane 1 being the unreduced α-N-acetylgalactosaminidase, lane 2 being the reduced α-N-acetylgalactosaminidase and lane 3 being the molecular weight standards (97.4, 66.2, 45.0, 31.0, 21.5, and 14.3 kDa)
Figure 9:
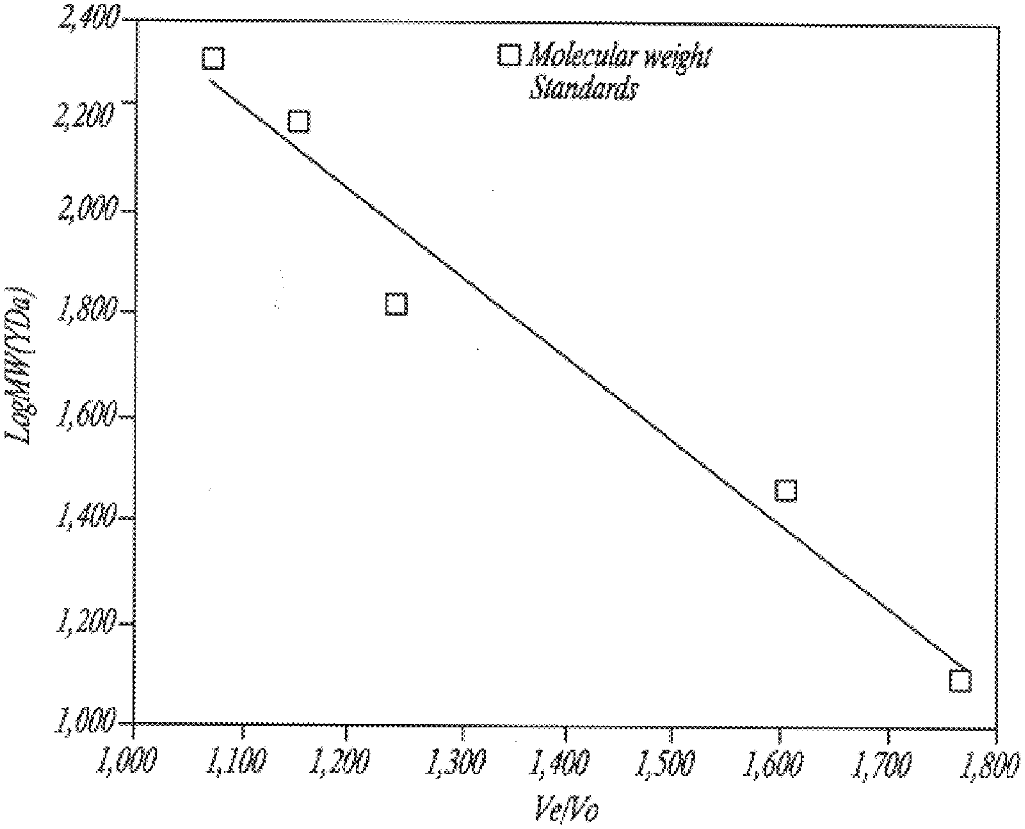
FIG. 9 shows a gel filtration wherein α-N-acetylgalactosaminidase is indicated by the arrow.
Figure 10:
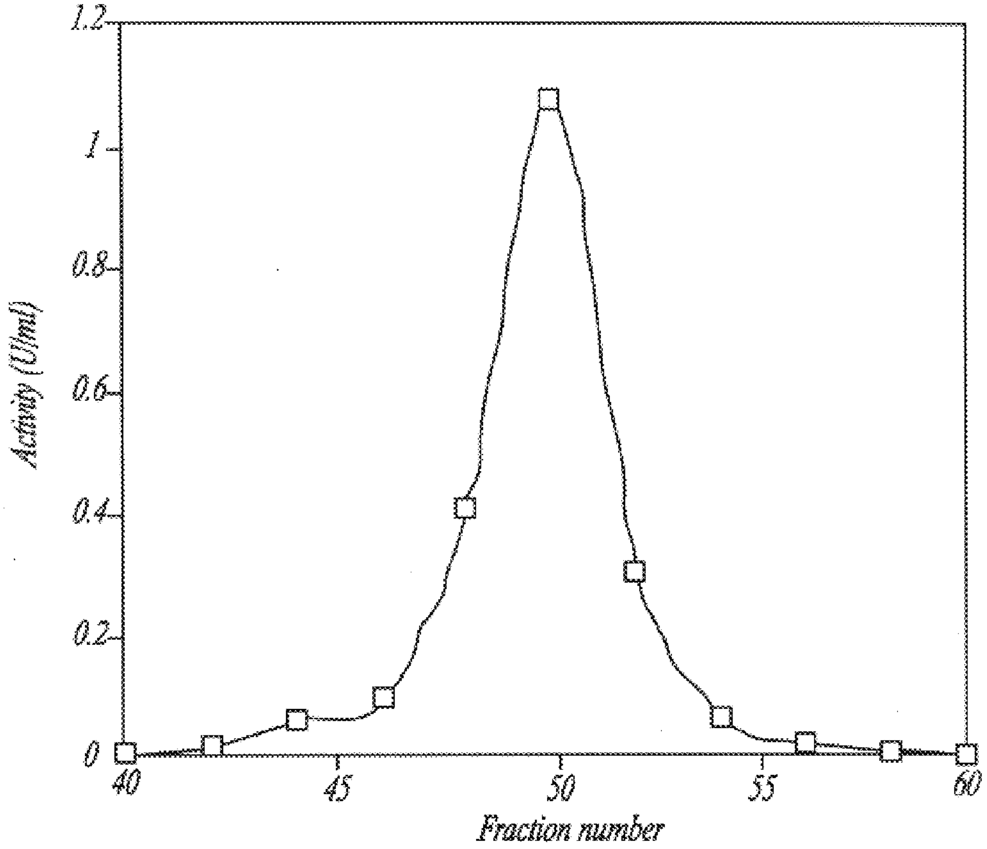
FIG. 10 shows a Hydroxyapatite HPLC wherein activity is shown with of U/ml being a function of fraction number.
Figure 11:
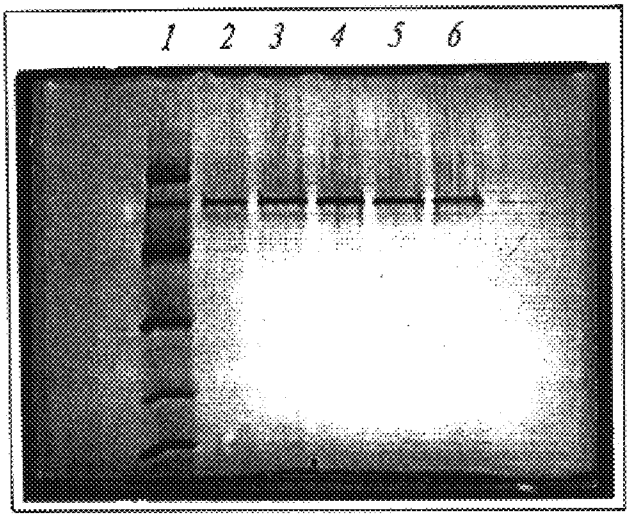
FIG. 11 shows an SDS-PAGE of column fractions with a zinc stain, lane 1 being the molecular weight standards (97.4, 66.2, 45.0, 31.0, 21.5, and 14.3 kDa) and lanes 2 through 6 showing the column fractions #48 to #52.

The purified preparation had a single detectable band when analyzed by Coomassie R-250 staining of a 12% SDS PAGE. The mean molecular weight, as determined by SDS-PAGE under reducing conditions, was 72.1 kDa (s.d.=1.1, n=6) as illustrated in FIG. 8. The mean native molecular weight was 57.5 kDa (s.d.=3.2, n=3) as calculated by gel filtration on Sephacryl S-200, FIG. 9. SDS-PAGE and enzymatic activity in the peak Hydroxyapitite HPLC fractions correlated with the staining intensity of the 72.1 kDa bands on the SDS PAGE, FIGS. 10 and 11. Amino acid composition data is presented in Table II. The molecular weight calculated from compositional data was 70.0 kDa.

In activity tests on a variety of substrates, specificity was shown for N-acetyl-α-D-galactosamine conjugates. Sugars, other than N-acetyl-α-D-galactosamine were poor substrates, Table III. The mean $K_m$ value for ONP-N-acetyl-α-D-galactosaminide and PNP-N-acetyl-α-D-galactosaminide were 1.58 (s.d.=0.07, n=3) and 1.35 (s.d.=0.01, n=3), respectively. The enzyme had a broad pH optimum at the range of 6.5 to 7.0, FIG. 12. The enzyme was not strongly inhibited by high or low ionic strengths at pH 7.0, FIG. 13.

No proteolytic activity was detected in the purified preparations. Aminopeptidase activity was below the limits of detection, <0.005 U $mg^{-1}$ enzyme, with the following substrates: PNA-alanine, PNA-lysine, PNA-leucine, PNA-proline, and PNA-valyl-alanine. In a resorufin-labeled casein protease assay with a sensitivity limit of 0.01 trypsin BABE units, there was less than 0.01 BAEE U $mg^{-1}$ enzyme detected. This corresponded to less than 0.78 ng of "trypsin-like activity" per mg of pure enzyme. The enzyme was also tested by an ELISA on human $A_2$ erythrocyte membranes. Removal of the terminal N-acetyl-α-D-galactosamine residue from the blood group A epitope was achieved by the enzyme as shown in FIG. 14.

Discussion

α-N-acetylgalactosaminidase from *Clostridium perfringens* was purified approximately 137-fold and was homogeneous by SDS-PAGE. In a previous report (Levy and Aminoff, 1980), it was hypothesized that the Clostridium enzyme was a multienzyme complex. SDS-PAGE and modular size exclusion chromatography implied that the enzyme in our preparations was monomeric and of lower molecular weight than Levy and Aminoff's estimate. The preparations observed by those authors, contained numerous bands when analyzed by SDS-PAGE. By the present method, the most significant contaminant, neuraminidase, was efficiently removed by the a combination of DEAE Sephadex A-50, SP Sephadex C-50 chromotagraphy, and PBE 94 chromatofocusing steps, the final purification was achieved by HPLC hydroxyapatite chromatography. This is critical and this purification has not been previously achieved. Accordingly, the use of the purified, isolated enzymes was limited. The present invention provides a high activity, isolated and purified enzyme with utility in the area of blood group alteration.

The enzyme was highly specific for the terminal α-N-acetylgalactosamine residues in glycosides, consistent with previous observation (Levy and Aminoff, 1980). The enzyme has no activity for p-nitrophenyl glycosides other than p-nitrophenyl-α-N-acetylgalactosamine. This is distinct from the achieved spectrum of the homogeneous preparations from human liver (Dean and Sweeley 1979) and from Acremonium sp. (Kadowaki et al, 1989) which exhibited α-N-acetylgalactosaminidase as well as α-galactosidase activity. Hence, the enzyme's utility is recognized for being highly specific in red blood cell type alteratives.

Eucaryotic α-N-acetylgalactosaminidases are lysozomal enzymes and have pH optima in the acidic range of 3.4–4.5 (Dean and Sweeley 1979; Kadowaki et al. 1989; Hata et al. 1992; Sung and Sweeley 1980). The *Clostridium perfringens* α-N-acetylgalactosaminidase shows functional activity in the range of physiological pH. This is an important property in respect to the possible use in enzymatic bioconversion technology, since it will allow cell membranes to be modified under physiologic pH conditions. In addition, the Clostridial enzyme may be particularly well-suited to the enzymatic conversion of blood group A to blood group O erythrocytes because the high activity is maintained at close to a neutral pH optima and over a wide range of ion strength, may allow unwashed red cell units to be used. The Clostridial enzyme is also useful for removing α-N-acetyl-D-galactosaminidase from other types of cells expressing the blood group A epitope, for example endothelial cells.

Preparations were free of proteolytic activity which is desirable if cells are to be used for transfusion as numerous erythrocyte antigens can be degraded by exogenous proteases (Wright 1989). Proteolytic modification create the potential for red cell clearance from the circulation. The activity of *Clostridium perfringens* α-N-acetylgalactosaminidase on group $A_2$ erythrocytes was tested by ELISA. The enzyme efficiently hydrolyzed the terminal N-acetyl-α-galactosamine residues from the blood group $A_2$ epitope.

*Clostridium perfringens* α-N-acetylgalactosaminidase can be used for enzymatic conversion of human blood group $A_2$ red cells to universally transfusable group O red cells. To obtain native enzyme in adequate yield is difficult, therefore, cloning of the α-N-acetylgalactosaminidase gene is used. Cloning can be accomplished by one skilled in the art by using known techniques. A recombinant *Clostridium perfringens* α-N-acetylgalactosaminidase expressed in high yields, is superior to the native lysozomal enzymes for biotechnical applications.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE I

Summary of *Clostridium perfringens* α-N-acetylgalactosaminidase purification

| Step | Total Volume (ml) | Total protein (mg) | Specific Activity (U/mg) | Total Units (U) | Yield (%) | Fold of Purity |
|---|---|---|---|---|---|---|
| Crude Extract | 2250.00 | 1177.50 | 0.32 | 376.92 | 100.00 | 1.00 |
| Ammonium Sulfate Precipitation | 76.67 | 204.44 | 0.53 | 107.93 | 28.63 | 1.65 |
| Sephacryl S-200 (I) | 483.33 | 72.50 | 0.84 | 60.97 | 16.18 | 2.63 |
| DEAE-Sephadex A-50 | 24.00 | 14.32 | 2.92 | 41.79 | 11.09 | 9.12 |
| PBE 94 Chromatofocusing | 54.00 | 1.08 | 19.73 | 21.31 | 5.65 | 61.65 |
| DEAE-Sephadex A-50 | 14.00 | 0.73 | 20.61 | 15.10 | 4.01 | 64.38 |
| Hydroxyapatite Type I | 3.73 | 0.17 | 43.92 | 7.43 | 1.97 | 137.20 |

*Data is expressed as the mean value of three different preparations.

TABLE II

Amino acid composition of *Clostridium perfringens* α-N-acetylgalactosaminidase

| | residues*/mole of protein |
|---|---|
| Asp & Asn | 51 |
| Ser | 53 |
| Glu & Gln | 81 |
| Gly | 51 |
| Arg | 28 |
| Thr | 28 |
| Ala | 32 |
| Pro | 17 |
| Tyr | 52 |
| Val | 33 |
| Met | 16 |
| Lys | 42 |
| Ile | 55 |
| Leu | 51 |
| Phe | 46 |

*Residue per mole of protein expressed in integer values

TABLE III

Substrate Specificity of *Clostridium perfringens* α-N-acetylgalactosaminidase

| Substrates | Activity (U/ml) |
|---|---|
| PNP-α-D-galactopyranoside | <0.001 |
| PNP-α-L-arabinopyranoside | <0.001 |
| PNP-β-D-galactopyranoside | <0.001 |
| PNP-N-acetyl-α-D-galactosaminide | 0.334 |
| PNP-N-acetyl-β-D-galactosaminide | <0.001 |
| PNP-α-D-glucopyranoside | <0.001 |
| PNP-β-D-glucopyranoside | <0.001 |
| PNP-N-acetyl-α-D-glucosaminide | <0.001 |
| PNP-N-acetyl-β-D-glucosaminide | <0.001 |
| PNP-α-L-fucopyranoside | <0.001 |
| PNP-β-L-fucopyranoside | <0.001 |
| PNP-α-D-mannopyranoside | <0.001 |
| 4MU-α-D-galactopyranoside | <0.001 |
| 4MU-N-acetyl-α-neuraminic aid | <0.001 |

*Data is expressed as the mean value of three independent duplicate determination.

TABLE IV

Kinetic Parameters of *Clostridium perfringens* α-N-acetylgalactosaminidase

| Substrate | Km |
|---|---|
| ONP-N-acetyl-α-D-galactosaminidase | 1.35 |
| PNP-N-acetyl-α-D-galactosaminidase | 1.58 |

*Data is expressed as the mean value of three independent determinations.

REFERENCES

Huston et al, 1991 "Protein engineering of single-chain Fv analogs and fusion proteins" in Methods in Enzymology (J J Langone, ed.; Academic Press, New York, N.Y.) 203:46–88.

Johnson and Bird, 1991 "Construction of single-chain Fvb derivatives of monoclonal antibodies and their production in *Escherichia coli* in Methods in Enzymology (J J Langone, ed.; Academic Press, New York, N.Y.) 203:88–99.

Mernaugh and Mernaugh, 1995 "An overview of phage-displayed recombinant antibodies" in Molecular Methods In Plant Pathology (RP Singh and US Singh, eds.; CRC Press Inc., Boca Raton, Fla.) pp. 359–365.

Economidou et al., "Quantitative measurements concerning A and B antigen sites" *Vox Sang.* 12:321–328 (1967)

Fong et al., "Developmental patterns of ABO isoagglutinins in normal children correlated with the effects of age, sex, and maternal isoagglutinins" *Transfusion* 14:551–559 (1974)

Goldstein et al., "Group B erythrocytes converted to group O survive normally in A, B, and O individuals" *Science* 215:168–170 (1982)

Goldstein, "Preparation of Transfusable Red Cells by Enzymatic Conversion", The Red Cell, 6th Ann Arbor Conf., 139–157 (1984)

Hata et al., "Purification and Characterization of N-Acetyl-α-D-Galactosaminidase", *Biochem. Intl.* 28:77–89 (1992)

Itoh and Uda, "α-N-Acetylgalactosaminidase from Squid Liver: Purification and Characterization of Two Enzymes", *J. Biochem.* 95:959–970 (1984)

Kadowaki et al., "Isolation and Characterization of Blood Group A Substance-degrading-α-N-Acetylgalactosaminidase from an Acremonium sp.", *Agri. Biol. Chem.* 53:111–120 (1989)

Kubo, "Changes in the specificity of blood groups induced by enzymes from soil fungi" *J. Forensic Sci.* 34:96–104 (1989)

Landsteiner, "Uber agglutination-serscheinungen normalen menschlichen blutes" *Klin. Wschr.* 14:1132 (1901)

McDonald et al., "α-N-Acetylgalactosa from Aspergillus niger", *Meth. Enzymol.* 28:735–738 (1972)

McGuire et al., "β-N-Acetylglucosaminidase, α-N-Acetylgalactos-aminidase and β-Galactosidase from *Clostridium perfringens* ", *Meth. Enzymol.* 28:755–763 (1972)

Mollison, "ABO, Lewis, Ii and P Groups", in *Blood Transfusion in Clinical Medicine*, (Blackwell Scientific Publications, London) pp. 267–327 (1987)

Nakagawa et al., "Purification and Characterization of α-N-Acetylgalactosaminidase from Skipjack Liver", *J. Biochem.*, 101:855–862 (1987)

Romano and Mollison, "Red cell destruction in vivo by low concentrations of IgG anti-A" *Br. J. Haematol* 29:121–127 (1987)

Schmidt, "The Mortality from Incompatible Transfusion", in *Immunobiology of the Erythrocyte* (Alan R. Liss Inc., New York) pp.251–261 (1980)

Wantanabe et al., "Status of Blood Group Carbohydrate Chains in Ontogenesis and in Oncogenesis", *J.Exp.Med.* 144:644–653 (1976)

Weissmann, "α-Acetylgalactosaminidase from Beef Liver", *Meth. in Enzymol.* 28:801–805 (1972)

Weissmann et al., "Mammalian α-Acetylgalactosaminidase. Occurrence, Partial Purification, and Action on Linkages in Submaxillary Mucins", *Biochem.* 8:2034–2043 (1969)

SEQUENCE LISTING

```
<160> NUMBER OF SEQ ID NOS: 1

<210> SEQ ID NO 1
<211> LENGTH: 29
<212> TYPE: PRT
<213> ORGANISM: Clostridium perfringens
<220> FEATURE:
<221> NAME/KEY: Xaa
<222> LOCATION: (1)..(29)
<223> OTHER INFORMATION: Xaa is any amino ac id

<400> SEQUENCE: 1

Met Lys Val Leu Gly Asn Tyr Ile Gln Arg A sn Phe His Tyr Asp Gly
1               5                   10                  15

Lys Xaa Phe Tyr Thr Lys Gln Phe Asn Lys P ro Ile Xaa
            20                  25
```

What is claimed is:

1. A method for isolating and purifying α-N-acetyl-D-galactosaminidase from *Clostridium perfringens* comprising the sequential steps of:

isolating enzymes from *Clostridium perfringens,* mixing into solution with $(NH_4)_2SO_4$, passing through a series of columns including passing through a column of SEPHACRYL S-200 (I) acrylic type organic substance column, passing through a column of DEAE SEPHADEX A-50 (I) ion exchange chromatography material column, passing through a column of PBE 94 exchanger a poly buffer exchanger for chromat focusing, passing through a column of SP SEPHADEX C-50 acrylic type organic substance column, passing through a column of DEAE SEPHADEX A-50 ion exchange chromatography material column, passing through a column of Hydroxyapatite Type I column, and collecting active fractions having passed through the column series wherein the fractions are pooled, concentrated, and dialyzed.

* * * * *